United States Patent
Toole

(12) 
(10) Patent No.: US 6,315,747 B1
(45) Date of Patent: Nov. 13, 2001

(54) POSTURE AID APPARATUS

(76) Inventor: James Patrick Toole, 9621 Baskerville, Rockwall, TX (US) 75087

( * ) Notice: Subject to any disclaimer, the term of this patent is extended or adjusted under 35 U.S.C. 154(b) by 0 days.

(21) Appl. No.: 09/624,700

(22) Filed: Jul. 24, 2000

(51) Int. Cl.[7] ................................................... A61F 5/00
(52) U.S. Cl. ..................................... 602/19; 128/DIG. 19
(58) Field of Search ................................. 602/5, 19, 20; 128/869, 876, DIG. 19

(56) References Cited

U.S. PATENT DOCUMENTS

| | | | |
|---|---|---|---|
| 3,718,137 | * 2/1973 | Gaylord | 128/DIG. 19 |
| 3,856,004 | * 12/1974 | Cox | 128/DIG. 19 |
| 3,857,388 | * 12/1974 | Frankel | 128/DIG. 19 |
| 3,897,776 | * 8/1975 | Gaylord | 128/DIG. 19 |
| 5,672,149 | * 9/1997 | Grundei | 128/DIG. 19 |

* cited by examiner

*Primary Examiner*—Michael A. Brown
(74) *Attorney, Agent, or Firm*—Martin Sachs, P.A.

(57) ABSTRACT

A therapeutic posture aid apparatus designed to properly align all three curves of the spine, hold the shoulder girdle in a proper posture position, allow full range of motion of all joints in the back, neck, shoulders and arms, reminding the wearer to move his/her back, neck and shoulders into a proper posture to eliminate/relieve, back pain, stress and muscle fatigue.

5 Claims, 2 Drawing Sheets

POSTURE AID APPARATUS

BACKGROUND OF THE INVENTION

1. Field of the Invention

The present invention relates orthopedic type braces, and more particularly, to a posture aid apparatus that can be worn comfortably, all the time, by an individual and will remind the wearer to move his/her back, neck and shoulders into the proper position to eliminate/relieve, back pain stress and muscle fatigue.

2. Discussion of the Relevant Art

The art abounds with inventions relating to devices for preventing the movement of the clavicle (collar bone) in a splint. One example of these devices is U.S. Pat. No. 3,382,868 issued to Henry K Stiefel on May 14, 1968.

Another device for providing a clavicle brace is disclosed in U.S. Pat. No. 4,570,619 issued to Paul B. Gamm on Feb. 18, 1986. The device disclosed therein includes adjustable straps and links in order to adjust the tension thereof for the comfort of the wearer thereof.

The present invention overcomes the shortcomings of the prior art devices by providing an orthopedic posture aid that can be worn all the time, and reminds the wearer thereof to correct his/her posture to eliminate back pain and fatigue.

Therefore, it is an object of the present invention to provide simple apparatus, that is non-adjustable, comfortable to wear and permits movement of the back and arms without irritation or pain.

It is another object of the present invention to provide a simple garment that can be readily worn un-detected beneath conventional garments.

Another object of the instant invention is to provide a relatively inexpensive apparatus to manufacture that requires simple care by the wearer.

Yet another object of the instant invention is to provide a relatively inexpensive apparatus that is sized, when purchased, to the individual that is to wear it.

Other and further objects and advantages of the invention will become apparent with the following detailed description of the invention.

SUMMARY OF THE INVENTION

An apparatus, according to the principles of the present invention, overcomes the shortcomings of the prior art by providing a reliable, effective, relatively inexpensive apparatus that will be able to be used by an individual (male or female), when properly sized under, conventional garments.

The foregoing and other objects and advantages will appear from the description to follow. In the description, reference is made to the accompanying drawing, which forms a part hereof, and in which is shown, by way of illustration, a specific embodiment in which the invention may be practiced. This embodiment will be described in sufficient detail to enable those skilled in the art to practice the invention and it is to be understood that other embodiments may be utilized and that structural changes may be made without departing from the spirit and scope of the invention. The following detailed description is, therefore, not to be taken in a limiting sense, and the scope of the present invention is best defined by the appended claims.

BRIEF DESCRIPTION OF THE DRAWING

In order that the invention may be more fully understood, it will now be described by way of example, with reference to the accompanying drawing in which.

DESCRIPTION OF THE PREFERRED EMBODIMENTS

Figure 1:
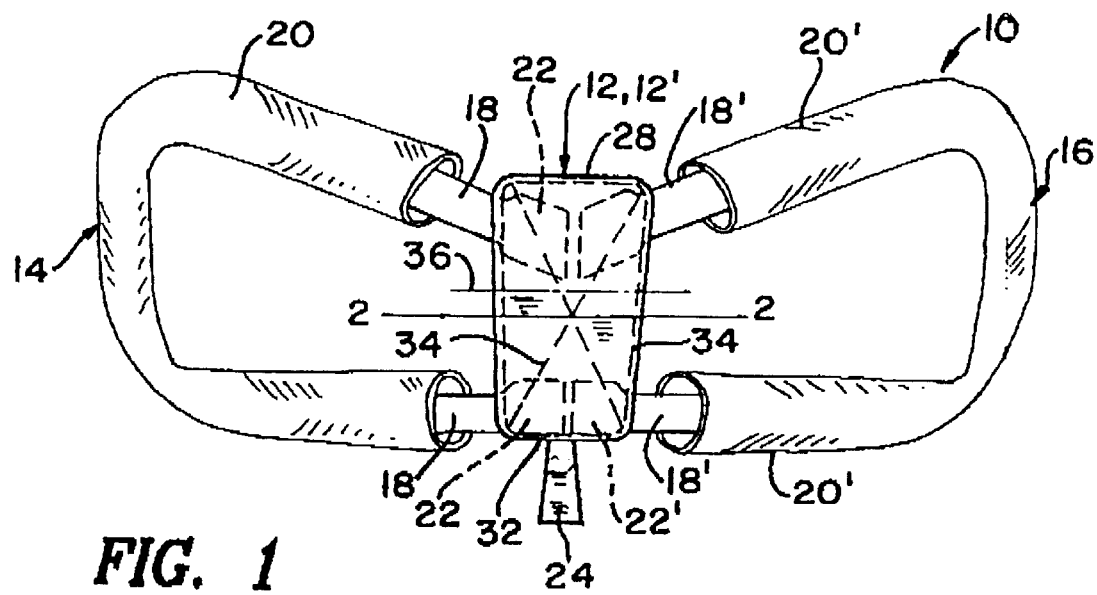
FIG. 1 is a pictorial view of a therapeutic posture aid apparatus, according to the principles of the present invention.

Referring now to the figures and in particular to FIG. 1, which shows the posture aid apparatus 10 having a hub member 12 and 12' that are centrally disposed between two arm members 14 and 16.

The arm members 14 and 16 are identical and are fabricated from an elongated elastic material 18 and 18' that is covered by a soft felt like material 20 and 20' that freely slides over the elastic material. Each one of the elastic arm members 14 and 16 has its elastic material 18 and 18' provided with larger end portions 22 and 22'.

A narrow extending tail member 24 is affixed to the lower portion of the hub member 12 and 12' and is cut to size so that the individual 26 that is wearing the posture aid apparatus can reach the tail member 24 and pull it down to position the hub member 12 directly between the shoulder blades.

The hub member 12 and 12' forms a sandwich with the end portions 22 of the elastic arm member 18 disposed so that one end thereof is positioned proximate the upper edge 28 parallel to the vertical axis 30 of hub member 12 and 12' and the other end 22 of the elastic arm member is disposed proximate the lower edge 32 parallel to the vertical axis 30 of hub member 12 and 12'. The end portions 22' of the other elastic arm member 18' disposed so that one end thereof is positioned proximate the upper edge 28 parallel to the vertical axis 30 of hub member 12 and 12' and the other end 22' of the elastic arm member is disposed proximate the lower edge 32 parallel to the vertical axis 30 of hub member 12 and 12'. The tail member 24 is disposed between the ends 22 and 22' of the elastic arm members 18 and 18'.

In order to insure that the end portions 22 and 22' of the elastic arm members 18 and 18' and one end of the tail member are permanently affixed to the hub members 12 and 12' stitching 34 is placed proximate the edges parallel to the vertical axis 30 and the horizontal axis 36, in addition to an "X" extending diagonally from one corner to the other of hub member 12 and 12'. The size of the posture aid apparatus 10 is chosen to be comfortably worn by the individual so that the arms 14 and 16 do not roll up and the arms of the individual do not tingle.

Figure 2:
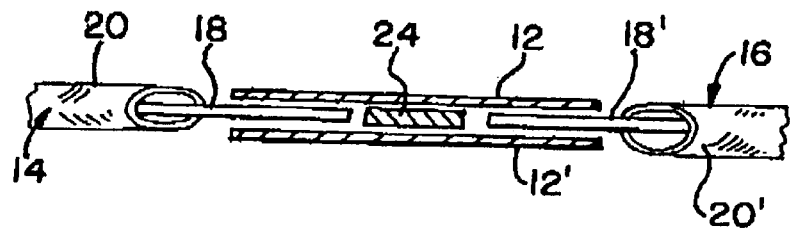
FIG. 2 is a cross-sectional view, in elevation, taken along the line 2—2 of FIG. 1.

Referring now to FIG. 2 there is shown a cross-section of the hub member taken along the line 2—2 of FIG. 1 showing the sandwiching of the tail member 24 and the elastic arm members 18 and 18' between the hub members 12 and 12'.

Figure 3:
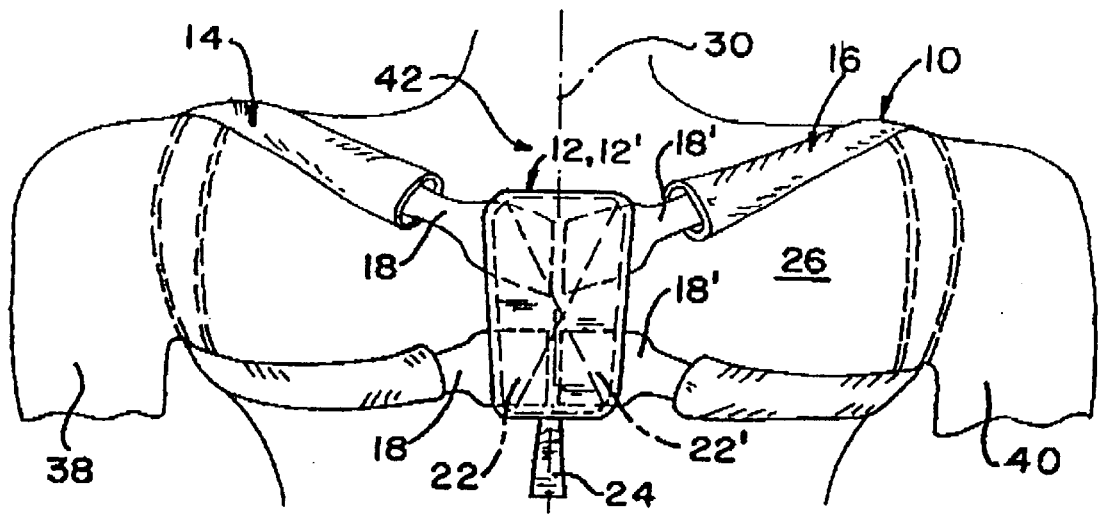
FIG. 3 is a rear view similar to FIG. 1, with the posture aid apparatus being in position on an individual.
Figure 4:
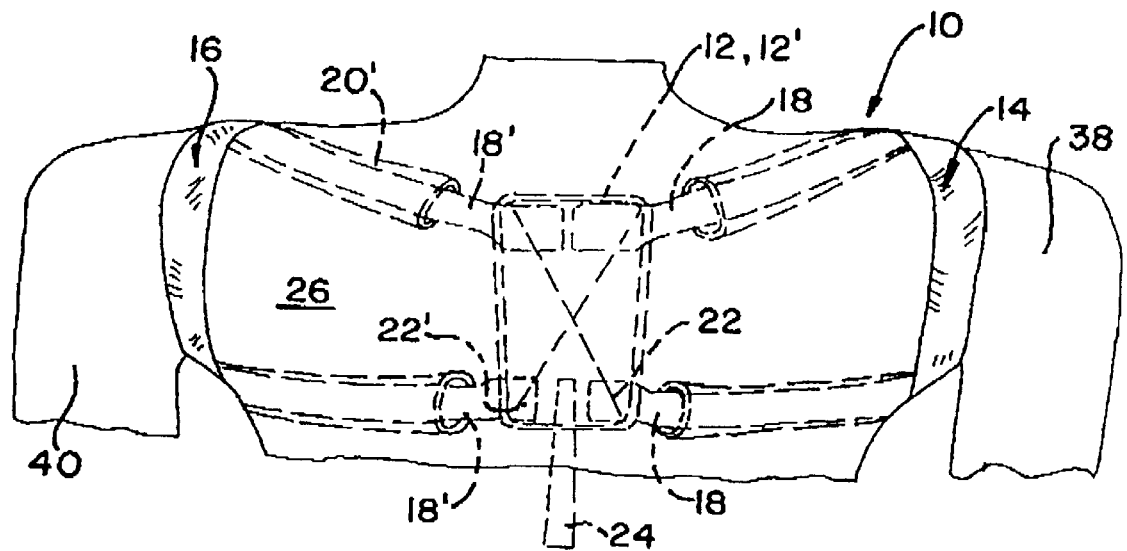
FIG. 4 is a front view, with the posture aid apparatus being in position on an individual.

Referring now to FIG. 3, wherein there is shown a pictorial rear view of the posture aid apparatus 10 positioned on a human 26 with the arms of the human having been fed through the arm members 14 and 16, respectively.

In operation, once the posture aid apparatus 10 has been selected in the proper size for the individual 26, one arm 38 is fed through the arm member 14 and the other arm 40 is fed through arm member 16 so that the vertical axis 30 of the hub member 12 is disposed upon the spinal column 42 of the individual 26, as shown in FIG. 3. If the posture aid apparatus is too high upon the back of the individual 26, the tail member 24 may be pulled down to lower the hub member 12, Hereinbefore has been disclosed a posture aid apparatus 10 that aligns all three curves of the spine and holds the shoulder girdle in proper position, allows full range of motion all joints of the back, neck, shoulders and arms, the wearer thereof. The apparatus 10 is fabricated from elastic so that an individual may put it on or remove it without assistance or adjustments and is covered with a soft material to increase comfort and eliminate binding.

It will be understood that various changes in the detail, materials, arrangements of parts and operating conditions which have been herein described and illustrated in order to explain the nature of the invention may be made by those skilled in the art within the principles and scope of the instant invention.

Having thus set forth the nature of the invention, what is claimed is:

1. A therapeutic posture aid apparatus comprising, in combination:
   A. a hub member having an elongated vertical axis with first and second edges generally parallel thereto and a transverse axis with two edges generally parallel thereto;
   B. a first elongated elastic member having two ends, the first end of said first elastic member being affixed to said hub member proximate the upper portion of said first edge parallel to said vertical axis, the other end of said first elastic member being affixed to said hub member proximate the lower portion of said said first edge parallel to said vertical axis;
   C. a second elongated elastic member having two ends, the first end of said second elastic member being affixed to said hub member proximate the upper portion of the second edge parallel to said vertical axis, the other end of said second elastic member being affixed to said hub member proximate the lower portion of said second edge parallel to said vertical axis; and
   D. a narrow extending tail member having two ends, one end thereof being affixed to said hub member proximate the lower transverse edge thereof.

2. A therapeutic posture aid apparatus, according to claim 1, further including first and second cover member means slideably covering said first and said second elastic members.

3. A therapeutic posture aid apparatus, according to claim 1, further including first and second cover member means for padding said first and said second elastic members.

4. A therapeutic posture aid apparatus, according to claim 1, wherein said hub member comprises two layers of material with said first and said second ends of said first and second elastic members being sandwhiched therebetween.

5. A therapeutic posture aid apparatus, according to claim 1, wherein said first and said second ends of said first and second elastic members are larger in width than the remaining portions of said elastic members.

* * * * *